US010682457B2

(12) United States Patent
Koch

(10) Patent No.: US 10,682,457 B2
(45) Date of Patent: Jun. 16, 2020

(54) DEVICE FOR TRANSFERRING A FLUID

(71) Applicant: Ulrich GmbH & Co. KG, Ulm (DE)

(72) Inventor: Torsten Koch, Neu-Ulm (DE)

(73) Assignee: ulrich GmbH & Co. KG, Ulm (DE)

(*) Notice: Subject to any disclaimer, the term of this patent is extended or adjusted under 35 U.S.C. 154(b) by 885 days.

(21) Appl. No.: 15/133,778

(22) Filed: Apr. 20, 2016

(65) Prior Publication Data

US 2016/0317735 A1 Nov. 3, 2016

(30) Foreign Application Priority Data

Apr. 30, 2015 (DE) .................... 20 2015 102 187 U

(51) Int. Cl.
*A61M 5/00* (2006.01)
*A61M 39/22* (2006.01)
(Continued)

(52) U.S. Cl.
CPC .......... *A61M 5/007* (2013.01); *A61M 5/1409* (2013.01); *A61M 39/22* (2013.01);
(Continued)

(58) Field of Classification Search
CPC .......... A61M 5/16804; A61M 5/16809; A61M 5/14224; A61M 2039/2446; A61M 5/1409; A61M 2205/123; A61M 2205/128; A61M 39/22; A61M 5/007; A61M 5/14; A61M 1/14; A61M 1/367; A61M 1/16; A61M 1/1601; A61M 39/26; A61M 2039/226;
(Continued)

(56) References Cited

U.S. PATENT DOCUMENTS 5,062,774 A 11/1991 Kramer et al.
5,738,662 A * 4/1998 Shannon ............. A61M 5/1408
137/606

(Continued)

FOREIGN PATENT DOCUMENTS

DE          10053441 A1   5/2002
DE          10239597 A1   3/2004
DE   10 2014 103 507 A1   9/2015

OTHER PUBLICATIONS

Result of search report for German Application No. 20 2015 102 187.9 dated Apr. 30, 2015.

*Primary Examiner* — Lauren P Farrar
*Assistant Examiner* — James D Ponton
(74) *Attorney, Agent, or Firm* — Paul D. Bianco; Stephen Bongini; Fleit Intellectual Property Law

(57) ABSTRACT

A device for transferring a fluid has a main channel, at least one secondary channel leading at an opening into the main channel, and a flexible closing element for closing the secondary channel. The opening of the secondary channel can be closed in a fluid-tight manner by the flexible closing element, by pressing the closing element with an external force onto or into the opening. In order to prevent that, in the case of a negative pressure in the main channel, the flexible closing element closes the secondary channel even without application of an external force, at least one projection is associated with the or each secondary channel and arranged in the main channel in the area of the opening of the respective secondary channel, and protrudes over the opening or over a lowest level of the opening.

20 Claims, 9 Drawing Sheets

(51) Int. Cl.
*A61M 5/14* (2006.01)
*F16K 7/16* (2006.01)
*F16K 27/02* (2006.01)

(52) U.S. Cl.
CPC ............ *F16K 7/16* (2013.01); *F16K 27/0236* (2013.01); *A61M 2039/226* (2013.01); *A61M 2205/12* (2013.01); *A61M 2205/123* (2013.01); *A61M 2205/128* (2013.01)

(58) Field of Classification Search
CPC .... A61M 2039/2433; A61M 2039/261; A61M 2039/262; A61M 2039/263; A61M 2205/12; A61M 2205/122; A61M 2005/1401; F16K 7/16; F16K 27/0236
See application file for complete search history.

(56) References Cited

U.S. PATENT DOCUMENTS

| | | |
|---|---|---|
| 6,752,172 B2 | 6/2004 | Lauer |
| 7,901,376 B2 * | 3/2011 | Steck ................ A61M 1/28 604/131 |
| 8,202,489 B2 | 6/2012 | Haecker et al. |
| 2002/0062109 A1 | 5/2002 | Lauer |
| 2005/0245889 A1 | 11/2005 | Haecker et al. |
| 2009/0012460 A1 * | 1/2009 | Steck ................ A61M 1/28 604/30 |
| 2011/0070132 A1 | 3/2011 | Haecker |

* cited by examiner

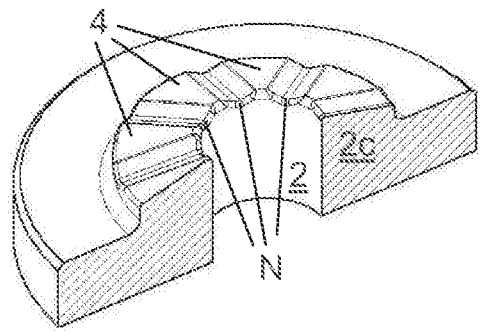
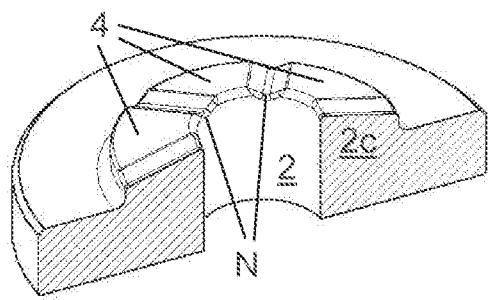
Fig. 9A    Fig. 9B
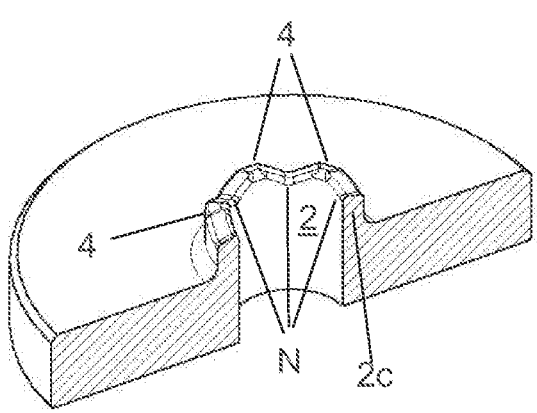
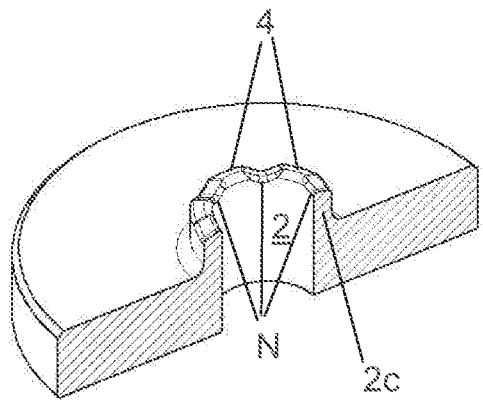
Fig. 9C    Fig. 9D

DEVICE FOR TRANSFERRING A FLUID

FIELD OF THE INVENTION

The invention relates to a device for transferring a fluid, to a cassette for insertion into a fluid-conveying device, in particular into an injection apparatus or a dialysis apparatus, which comprises such a device, as well as to a fluid-conveying device, in particular an injection apparatus or a dialysis apparatus having such a cassette.

BACKGROUND

A device for transferring a fluid is known from DE 100 53 441 A1, which describes a device for supplying and/or branching off a secondary flow into or from a main flow of a medicinal fluid. The device here comprises a fluid-conveying body, in which a main channel which is open to one side and at least one secondary channel leading into the main channel are formed. The open side of the main channel is covered by a cover film, and the opening of the secondary channel into the main channel can be closed by the cover film. For closing the opening of the secondary channel, the cover film can be pressed by a valve actuator onto the opening of the secondary channel. This device can be used, for example, in an exchangeable cassette to be inserted into a fluid-conveying device such as an injection apparatus or a dialysis apparatus, for example. The valve actuators for closing the opening of the secondary channel are arranged here in the fluid-conveying device, and the cassette is inserted therein so that the valve activators come to be applied on opening sites where a secondary channel leads into the main channel, so that the openings of the secondary channels can be closed (alternately) due to an actuation of the valve actuators.

In the known transfer devices, one problem is, in the case of a negative pressure in the main channel or in a secondary channel, the cover film, which can be designed as a film or as a resilient membrane made from an elastomer material, can be pulled onto the opening of a secondary channel, even if the associated valve actuator is not actuated. Subsequently, it may happen that the secondary channel is closed unintentionally even if the valve actuator is not activated, due to a negative pressure in the main channel or the secondary channel. In a corresponding manner, when opening closed secondary channel openings, problems can also occur if a negative pressure develops in the area of the main channel or of the secondary channel. This can occur, for example, in the case of an actuated valve actuator and closed opening of a secondary channel, if the conveyance pump by means of which the fluid is conveyed through the channel still continues to run for a short time after the pump has been switched off. In the case of an unintentional opening of the sealing seat of the cover film on an opening of a secondary channel by actuating the valve actuator into its open position, it may occur that the cover film does not separate from its sealing seat on the opening surface of the secondary channel, due to the negative pressure in the secondary channel, and the secondary channel therefore remains unintentionally closed.

SUMMARY OF THE INVENTION

Based on this, at least some embodiments of the invention ensure, in a device for transferring a fluid, a reliable opening and closing of the opening of a secondary channel, without the possibility of an unintentional closing of the secondary channel opening, which can be caused, for example, by a negative pressure in the secondary channel or in the main channel.

Preferred embodiments of the device according to the invention for transferring a fluid are also disclosed herein.

The device according to the invention comprises a main channel and at least one secondary channel which leads at an opening into the main channel, and which can be used as supply channel for supplying a fluid from the secondary channel into the main channel. The device according to the invention moreover comprises a flexible closing element for closing the opening of the secondary channel, wherein the closing element can be pressed by means of an external force which can be provided, for example, by an external valve actuator, onto the opening of the secondary channel, in order to close the secondary channel opening in a fluid-tight manner. According to the invention, at least one projection, which is arranged in the main channel in the area of the opening of the respective secondary channel and which protrudes over the opening or at least over a lowest level of the opening, is associated with the or each secondary channel. The lowest level of the opening of a secondary channel here is understood to mean the opening area of the secondary channel which, in the direction of flow of the fluid in the secondary channel as first (downstream) area, leads into the main channel. By means of the or each projection it is ensured that, in the case of a negative pressure in the main channel or in the secondary channel, the flexible closing element cannot be pulled unintentionally onto the opening of the secondary channel, if no external force acts on the closing element. This is achieved in that, in the case of absence of an external force, the flexible closing element is pulled by any negative pressure that may prevail in the main channel or in the secondary channel only at most to the downstream upper side of the or each projection of a secondary channel, without the flexible closing element being able to reach the area of the opening of the secondary channel or the area of the lowest level of the opening. As a result, the opening of the secondary channel remains open, at least in the area of the lowest opening level, even if the flexible closing element is pulled by the negative pressure prevailing in the main channel or in the secondary channel against the direction of flow of the fluid in the secondary channel in the direction of the opening of the secondary channel. The opening of the secondary channel can only be closed (completely) by a sufficiently large external force, which presses the closing element for closing the secondary channel into or onto its opening. Here, the flexible closing element is advantageously pressed both onto the or each projection of the respective secondary channel as well as onto its opening margin, in order to generate a fluid-tight closing of the secondary channel.

The or each projection associated with a secondary channel turns out to be also advantageous in the case of an unintentional opening of the opening of the secondary channel. For example, if, as a result of continued running of a conveying pump which conveys a fluid through the device according to the invention, there is still some additional run after the pump has been turned off, it may happen that a low pressure develops in the main channel, in particular in the flow area around a secondary channel. If a secondary channel that has been closed intentionally by application of an external force onto the flexible closing element is now to be opened by removing the external force, the or each projection of this secondary channel assists in causing the separation of the closing element from its sealing seat on the opening of the secondary channel, separation which is caused by the intrinsic flexibility of the closing element. As a result of the assistance of the or each projection, the flexible closing element can thus become separated more easily from the sealing seat on the opening of the secondary channel, due to a resetting force caused by the resilience properties of the closing element, even if a possible negative pressure acts against this opening movement of the closing element. As a result, it is ensured that the opening and closing of the secondary channel occurs exclusively by the separation or the application of an external force on the flexible closing element and is not dependent on a negative pressure that may have developed in the main channel or in the secondary channel.

The flexible closing element is, for example, a flexible film or a flexible membrane made, in particular, from a thermoplastic elastomer that has a sufficiently high flexibility and ductility in order to be pressed onto the opening of a secondary channel by means of an external force which can be provided, for example, by a movable valve actuator. The resilient and flexible properties of the closing element here are selected so that the closing element provides a sufficiently high intrinsic resetting force, which automatically brings the flexible closing element into a base position, if no external force is acting on the closing element, wherein, in the base position of the closing element, the opening of the secondary channel is open.

In an embodiment example of the device according to the invention, the main channel and each secondary channel are formed in a body, and the main channel comprises, at least at the sites opposite from an opening of a secondary channel, an opening which is covered by the flexible closing element. The body can be, for example, an injection molded plastic housing part of a cassette, which is provided for insertion into a fluid-conveying device such as, for example, into an injection apparatus or a dialysis apparatus. Here, it is possible that the main channel is open toward one side along its longitudinal direction and completely covered on the open side by the flexible closing element, which then has a flat form, for example, the form of a membrane or a film. However, it is also possible to provide an opening in the main channel only in the areas in which a secondary channel leads into the main channel, opening which is designed in the shape of a circle, for example, and which is opposite from the opening of the secondary channel. This opening in the main channel is covered here by a flexible closing element, for example, by a plate-shaped membrane which can be pressed by application of an external force onto the opening of the secondary channel, in order to close the secondary channel.

For insertion of the cassette with the device formed therein according to the invention into a fluid-conveying device such as, for example, an injection apparatus or a dialysis apparatus, it is advantageous to provide, for each secondary channel, a movable valve actuator in the fluid conveyance direction, which provides the external force for pressing the closing element onto the opening of the secondary channel. Here, the valve actuator in each case is movable between a closed position and an open position, wherein the valve actuator presses the closing element in its closed position onto or into the opening of the secondary channel. In the open position of the actuator, the flexible closing element is in its base position in which the opening of the secondary channel is open, so that the fluid can flow from the secondary channel into the main channel (or also in the opposite direction from the main channel into the secondary channel).

In preferred embodiment examples of the invention, at least two projections are associated with each secondary channel of the device according to the invention. The projections here are advantageously arranged distributed evenly around the opening of the respective secondary channel. The opening of the or each secondary channel can be formed, for example, by the open end of a cylindrical tube which protrudes into the main channel. The longitudinal axis of the main channel and the longitudinal axes of the supply channels can here be approximately perpendicular to one another. However, it is also possible that a secondary channel leads at an acute angle into the main channel.

Advantageously, in the area of a discharging secondary channel, the main channel is formed as ring channel which extends in the shape of a ring around a cylindrical channel wall of the secondary channel. As a result, a flow promoting shaping of the main channel and of the secondary channel discharging into it is ensured, which does not impede the flow of the fluid in the main channel. In particular, a laminar and largely resistance-free flow of the fluid in the main channel is ensured. However, the shape of the cross section of the or each secondary channel can also be designed differently. It is advantageous here to use streamlined outer contours of the channel walls of the respective secondary channel, which engage into the main channel, as proposed, for example, in DE 100 53 441 A1.

In order to ensure a reliable fluid-tight closing of a secondary channel by means of a flexible closing element, it has been found to be advantageous to place the opening or the lowest level of the opening of the or each secondary channel in the area of the center plane of the main channel.

The distance between the downstream upper side of the or each projection, and the opening or the lowest level of the opening of the associated secondary channel is advantageously designed so that, in the case of a possible negative pressure in the main channel or in the secondary channel, which can be generated, for example, by a fluid-conveying pump of a fluid-conveying device, the closing element is in fact applied on the downstream upper side of the or each projection, but not on the opening of the secondary channel or its lowest opening level.

For the design of the or each projection, streamlined outer contours have been found to be advantageous, so that the flow in the main channel is not impeded by the or each projection. In particular, the projections can be designed in the form of a pin, column, dome or mushroom. The projections associated with the secondary channel are here advantageously arranged at a distance from the outer diameter of the discharge opening of the secondary channel. However, it is also possible to arrange the or each projection of a secondary channel on the upper margin of the wall of this secondary channel, so that the or each projection can directly abut against the outer diameter of the discharge opening. However, an arrangement of the projections of a secondary channel at a distance from the outer diameter of the discharge opening is preferable, since, as a result, a better closing of the discharge opening can be ensured, if the closing element is in its closed position. In the closed position, the closing element is applied here both on the downstream upper side of the or each projection of a secondary channel and also on its opening margin, in order to ensure a reliable and fluid-tight closing of the secondary channel.

BRIEF DESCRIPTION OF THE DRAWINGS

These and additional advantages of the device according to the invention as well as application examples result from the embodiment examples described below in reference to the accompanying drawings, examples in which a device according to the invention for transferring contrast agent solutions and a rinsing solution in an injection system for intravenous injection of these solutions into the human or animal body is represented. The device according to the invention here is a component of a cassette for insertion into an injection device. However, the use of the invention is not limited to this embodiment example which merely describes as an example the features and advantages of the invention. The drawings show:

FIGS. 9A-9D: perspective sectional views of additional embodiments of the device according to the invention with several projections arranged on the channel wall of a secondary channel leading into the main channel;

DETAILED DESCRIPTION

Figure 1:
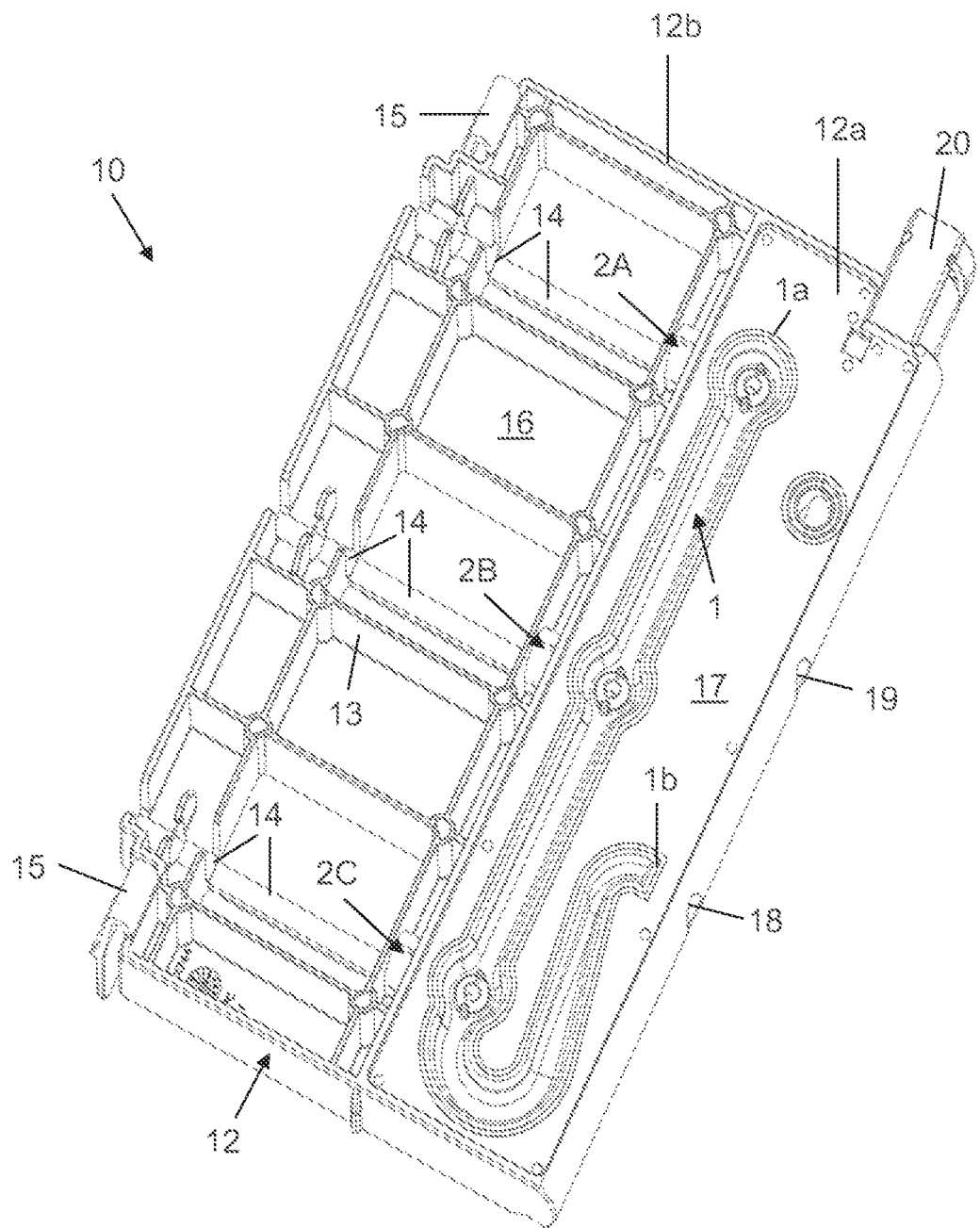
FIG. 1: a perspective representation of a cassette for insertion into an injection device, wherein the cassette contains a device according to the invention for transferring a fluid, with a main channel and several secondary channels leading into said main channel.

In FIG. 1, in a perspective top view, a cassette 10 for insertion into a fluid-conveying device, not shown here, in the form of an injection device is shown. The cassette 10 comprises a body 12 in which a device according to the invention for transferring a fluid is formed. The body 12 can be, for example, an injection molded plastic part made of a hard plastic such as PC or other plastics such as PE or PP. The body 12 has a bottom 16, on which protruding side walls 13 and reinforcing webs 13' are formed. The body is divided into a first section 12a in which the device according to the invention is arranged, and a second section 12b in which several hose entries 14 for inserting flexible supply hoses are provided. Moreover, in the second section 12b of the body 12, an attachment device 15 for attaching the cassette 10 in the injection device is arranged.

In the first section 12a of the body 12, flow channels are arranged in the bottom 16, namely a main channel 1 which extends substantially in the longitudinal direction of the first section 12a of the body 12 and parallel to the bottom 16. The upper side of the main channel 1, which faces away from the bottom side of the floor 16, has an open design and is covered by a closing element 3 not shown in FIG. 1. The closing element 3 is a flexible membrane or a flexible film, which is applied on the upper side 17 of the first body section 12a, which faces away from the floor 16 and is attached there, for example, by gluing or by welding.

Moreover, in the solid material of the first section 12a of the body 12, several secondary channels 2 are formed, which lead in each case at one end into the main channel 1. In the embodiment example represented in FIG. 1, three secondary channels 2A, 2B, 2C are provided. The first secondary channel 2A leading at the upstream end 1a into the main channel 1 is used for supplying a rinsing solution such as, for example, a saline solution, into the main channel 1. For this purpose, the other end of the first secondary channel 2A is connected via a supply hose to a container containing a rinsing solution. The other two secondary channels 2B, 2C, which lead downstream into the main channel 1, are used for supplying contrast agent solutions into the main channel. For this purpose, the other ends of the two secondary channels 2B, 2C in each case are also connected via a supply hose to a container which contains a contrast agent solution. The inner diameter of the secondary channels 2 is advantageously in the range of 2 to 4 mm and preferably approximately 3 mm. The diameter of the main channel 1 is advantageously slightly larger and it is preferably in the range of 3 to 6 mm.

Figure 3A:
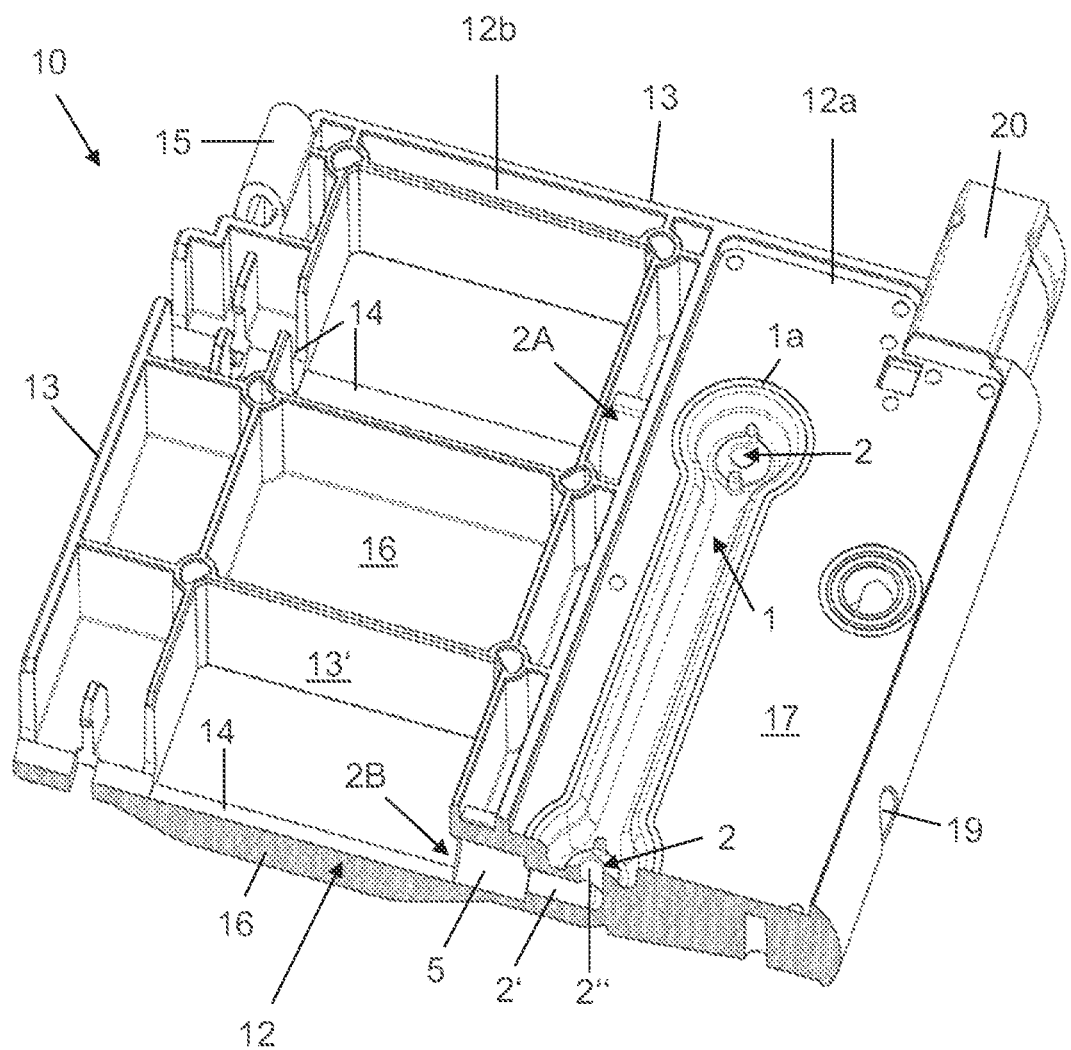
FIG. 3A: a perspective sectional view of the cassette of FIG. 1 in the area of a secondary channel leading into a main channel, with a section plane in transverse direction to the main channel.
Figure 3B:
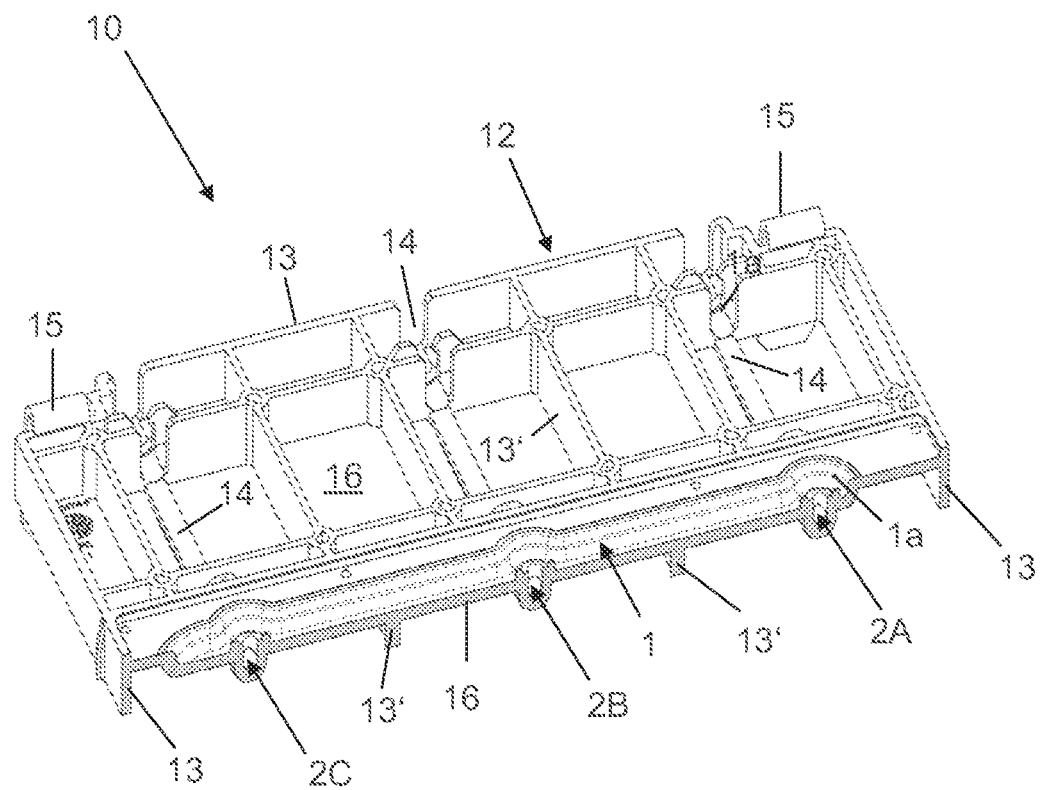
FIG. 3B: perspective sectional view of the cassette of FIG. 1 in the area of a secondary channel leading into a main channel, with a section plane in longitudinal direction of the main channel.

In the sectional view of FIGS. 3A and 3B, the shape of the secondary channel 2B can be seen in the section plane. Said secondary channel—like the other secondary channels 2A, 2C—has an upstream first section 2', which extends substantially parallel to the floor 16 of the cassette 10, as well as a second section 2" connected to the first section 2', which is designed in the form of a bore extending perpendicularly to the first section 2' and perpendicularly to the main channel 1, in the solid material of the body 12, and leads into the main channel 1. At the end of the first section 2', which faces away from the second section 2", in each secondary channel 2, a connection piece 5 is arranged, which is used for connecting a supply hose not represented here. A supply hose connected at one end to the connection piece 5 is connected at the other end to a storage container for a fluid, for example, a contrast agent solution or a rinsing solution.

At the downstream end 1b of the main channel 1, a connection 18 for connecting a pump hose, not represented, is provided here. An end of the pump hose is connected for the operation of the cassette 10 to the connection 18, and the other end of the pump hose is connected to an additional connection 19 arranged in the first section 12a of the body 12, so that the pump hose protrudes in the form of a loop or half circle from the body 12 of the cassette 10. The connection 19 is connected to a discharge channel which is formed in the body and not visible in the figures, and whose downstream end has a connection 20 for connection to a patient hose not represented here. At one end, the patient hose is connected to the connection 20 and at the other end to a cannula, which is introduced for intravenous injection of the fluid transferred with the cassette 10 for intravenous administration of the fluid conveyed in the main channel 1 into a vein of a patient.

Figure 2:
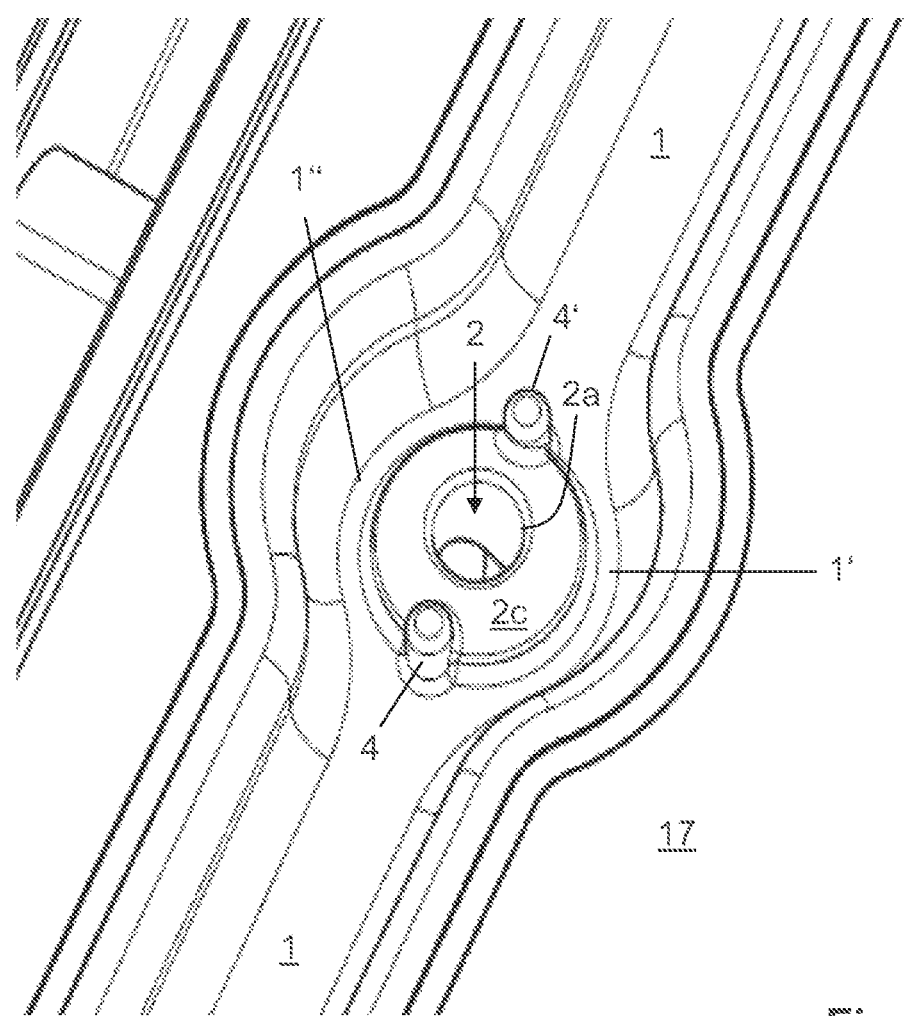
FIG. 2: a detail view of the main channel of the cassette of FIG. 1 in the area of a discharging secondary channel.

In FIG. 2, the opening 2a of a secondary channel 2 in the main channel 1 is represented in detail. The second section 2" of this secondary channel 2, which extends at least approximately perpendicularly to the main channel 1, has a tubular channel wall 2c, which leads into the main channel 1. Advantageously, the opening 2a of the secondary channel 2, which is formed by the upper margin of the tubular 2, is located at least approximately in the area of center plane of the main channel 1. In the area of the opening 2a of the secondary channel 2, the main channel 1 is designed as a ring channel with two ring channel sections 1', 1". The two ring channel sections 1', 1" here extend in the shape of a ring around the channel wall 2c of the secondary channel 2.

In the area of the channel wall 2c of the secondary channel 2, in the embodiment example depicted in the drawing here, two projections 4, 4' are arranged, which are designed cylindrically or in the shape of a dome or a column and which protrude like the channel wall 2c into the main channel 1. The two projections 4, 4' here are arranged at diametrically opposite sites of the opening 2a and they protrude over the opening 2a of the secondary channel 2, as can be seen in FIGS. 4-6. The top side of the two projections 4, 4' is thus located in the direction of flow of the fluid in the second section 2" of the secondary channel 2 viewed in comparison to the opening 2a on a downstream level and thus protrude over the level N of the opening 2a. This is indicated diagrammatically in FIG. 7A. The projection between the level N of the opening 2a and the top side of the projections 4, 4' is advantageously between 0.3 and 0.7 mm and preferably approximately 0.5 mm.

Figure 4A:
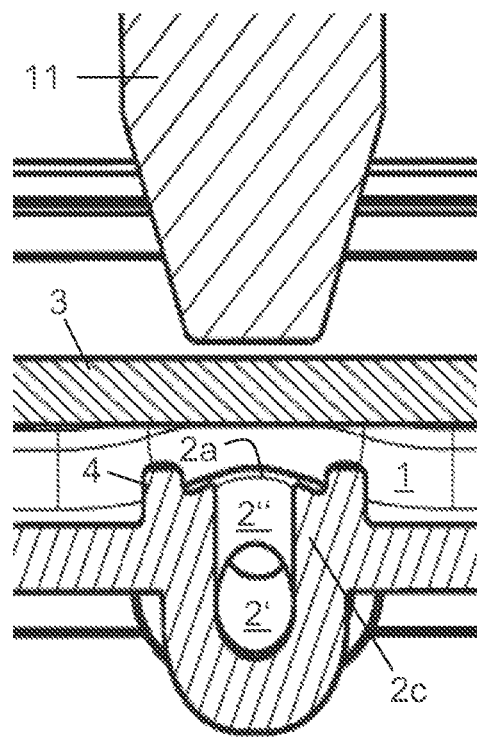
FIG. 4A: a detail view of the section plane of the cross section of FIGS. 3A and 3B in the area of the opening of the secondary channel in a front view onto the section plane together with a closing element not shown in FIGS. 1-3 for closing the secondary channel, and a valve actuator for generating an external force with which the closing element can be pressed onto the opening of the secondary channel, wherein the closing element is shown in a base position and the valve actuator is shown in an open position.
Figure 4B:
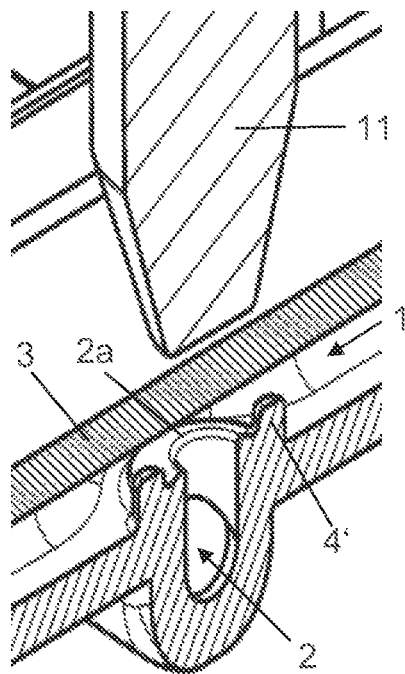
FIG. 4B: a detail view of the section plane of the cross section of FIGS. 3A and 3B in the area of the opening of the secondary channel in a perspective view onto the section plane together with a closing element not shown in FIGS. 1-3 for closing the secondary channel, and a valve actuator for generating an external force with which the closing element can be pressed onto the opening of the secondary channel, wherein the closing element is shown in a base position and the valve actuator is shown in an open position.
Figure 5A:
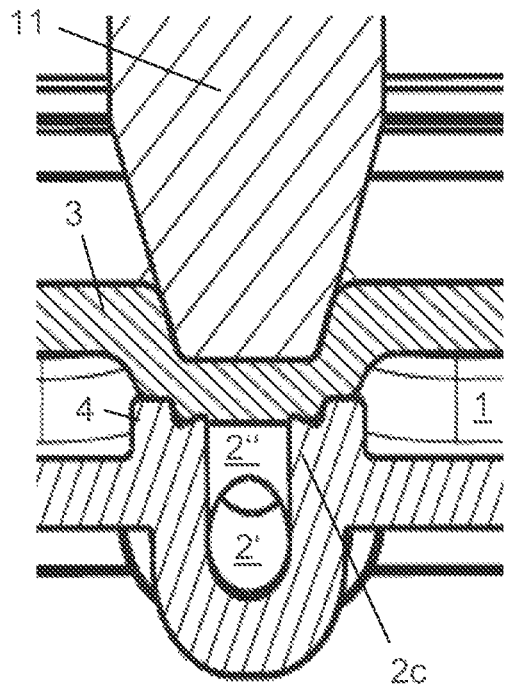
FIGS. 5A and 5B: a cross-sectional view of the secondary channel of FIGS. 4A and 4B, wherein the valve actuator is shown in a closed position in which it presses the closing element into a closing position onto the opening of the secondary channel.
Figure 5B:
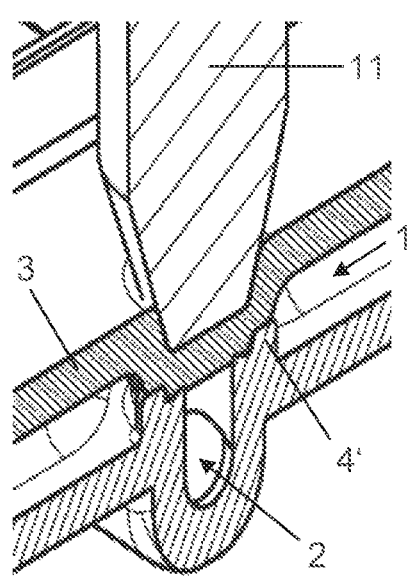

The function of the device according to the invention for transferring a fluid and in particular of the projection flows 4, 4' can be obtained from the drawings of FIGS. 4-6. In FIGS. 4-6, a secondary channel 2 leading into the main channel 1 is represented in cross section together with the flexible connection means 3 for closing the secondary channel 2 and a valve actuator 11. The valve actuator 11 here is a component of a fluid-conveying device, for example, of an injector, into which the cassette 10 is inserted. The valve actuator 11 is movable here between an open position shown in FIGS. 4A and 4B and a closed position shown in FIGS. 5A and 5B. For moving the valve actuator 11 between its open position and its closed position, said valve actuator is coupled to a driving means not shown here. The valve actuator 11 is used here to press the flexible closing element 3 for closing the secondary channel 2 onto or into the opening 2a of the secondary channel.

In the representation of FIGS. 5A and 5B, the valve actuator 11 is in its open position, in which it does not exert a force on the flexible closing element 3. The closing element 3 is located accordingly in a base position, in which the closing element 3 is arranged at a distance from the opening 2a of the secondary channel 2. The distance between the bottom side of the closing element 3 and the opening 2a of the secondary channel 2, in the base position, is advantageously between 1 and 2 mm and preferably approximately 1.8 mm. The opening 2a of the secondary channel 2 is open in this base position of the closing element 3, so that a fluid supplied through the first section 2' into the secondary channel 2 can flow via the second section 2" from the opening 2a of the secondary channel 2 into the main channel 1. The valve formed by the interaction of the flexible closing element 3 and the valve actuator 11 is open in this base position of the closing element 3.

In FIGS. 4A and 4B, the valve is shown in its closed position. Here the valve actuator 11 is in its closed position, in which it exerts an external force onto the flexible closing element 3. This force presses the closing element 3 onto the opening 2a of the secondary channel 2, as a result of which said opening is closed in a fluid-tight manner. The closing element 3 is in a closed position, in which the closing element 3 bears both against the opening 2a of the secondary channel 2 (on the upper margin of the channel wall 2c) and at the same time against the upper side of the projections 4, 4'.

Figure 6A:
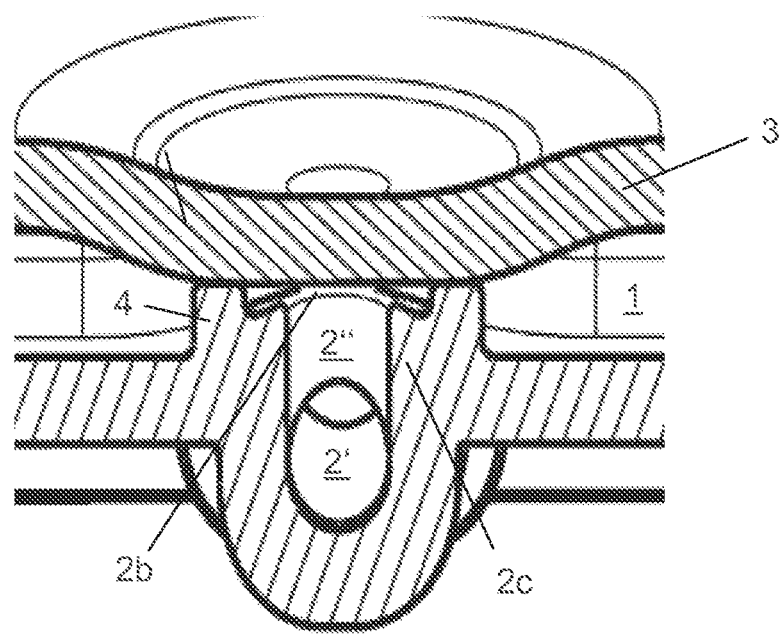
FIGS. 6A and 6B: a cross-sectional view of the secondary channel of FIGS. 4A and 4B, wherein the closing element is located in an intermediate position between the open position of FIGS. 4A and 4B and the closed position of FIGS. 5A and 5B, while the valve actuator not shown is in its open position.
Figure 6B:
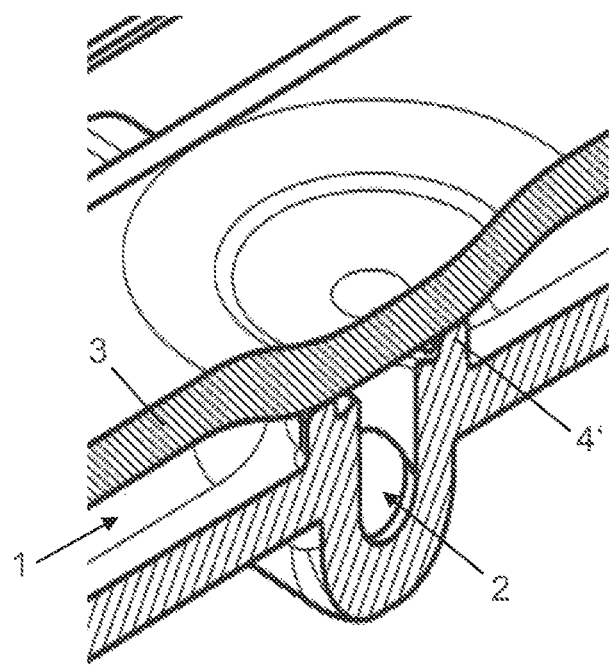

In FIGS. 6A and 6B, the flexible closing element 3 is shown in an intermediate position between its base position and its closed position. The valve actuator 11, which is not represented in FIGS. 6A and 6B, is here in its open position. The intermediate position shown in FIGS. 6A and 6B is assumed by the flexible closing element 3, for example when a negative pressure has developed in the main channel 1 or in the secondary channel 2, which leads to the closing element 3 being pulled from its base position in the direction of the opening 2a of the secondary channel 2. A negative pressure forming in the main channel 1 or in the secondary channel 2 exerts a tensile force on the flexible closing element 3, which pulls the latter in the direction of the opening 2a of the secondary channel. However, the negative pressure caused by the tensile force is not as large as the compressive force exerted by the valve actuator 11 on the closing element 3, if the valve actuator 11 is in its closed position. The flexible closing element 3 is therefore pulled by the tensile force only into the intermediate position shown in FIGS. 6A and 6B. In this intermediate position, the bottom side of the flexible closing element 3 is applied on the upper side of the projections 4, 4', without establishing a contact with the opening 2a (that is to say the upper side of the channel wall 2c) of the secondary channel 2. In this intermediate position, the opening 2a of the secondary channel 2 is open although a tensile force (caused by a negative pressure, for example) is exerted on the flexible closing element 3. In this state, with open valve, a fluid can flow from the secondary channel 2 through the opened opening 2a into the main channel 1, and a pressure compensation between main channel and secondary channel can occur. This is the result of the fact that the flexible closing element 3 cannot be pulled by the tensile force up to the opening 2a of the secondary channel 2, due to the application on the upper side of the projections 4.

In this way, the projections 4 ensure that, even if a negative pressure develops in the main channel 1 and/or in the secondary channel 2, a complete closing of the opening 2a of the secondary channel 2 cannot occur, if the valve actuator 11 is in its open position. Conversely, during the opening of the valve, due to the movement of the valve actuator 11 from its closed position into its open position, the projections 4, 4' ensure an improved raising of the closing element 3 from the opening 2a of the secondary channel 2. Even if a negative pressure prevails in the main channel 1 or in the secondary channel 2, the flexible closing element 3 can move automatically into its base position due to its intrinsic resilience and the resulting resilient resetting force. This movement is supported here by the projections 4.

Figure 7A:
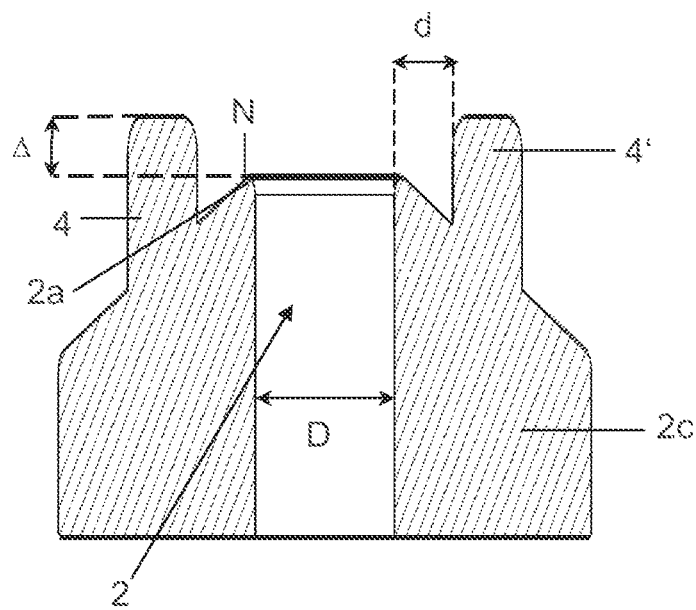
FIGS. 7A and 7B: a representation of an embodiment of the device according to the invention with two projections in the area of a secondary channel leading into the main channel in a sectional view (FIG. 7A) and in a perspective sectional view (FIG. 7B)
Figure 7B:
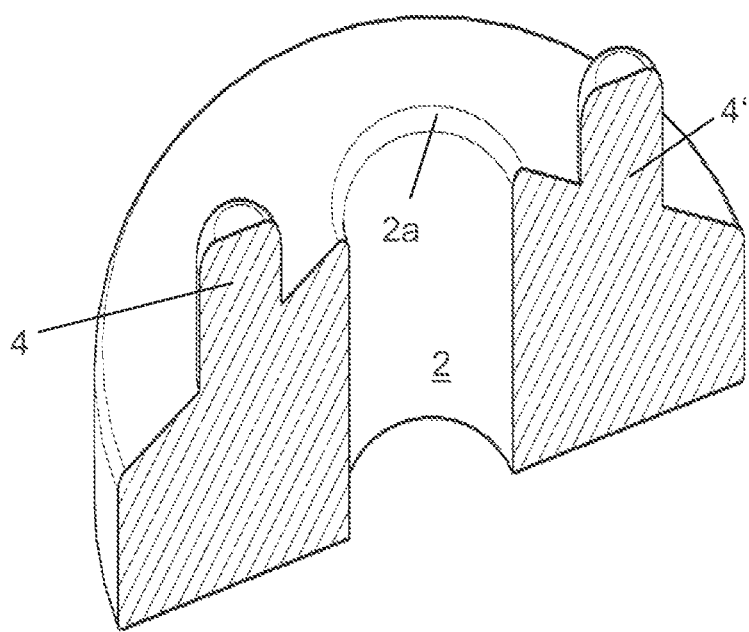
Figure 8A:
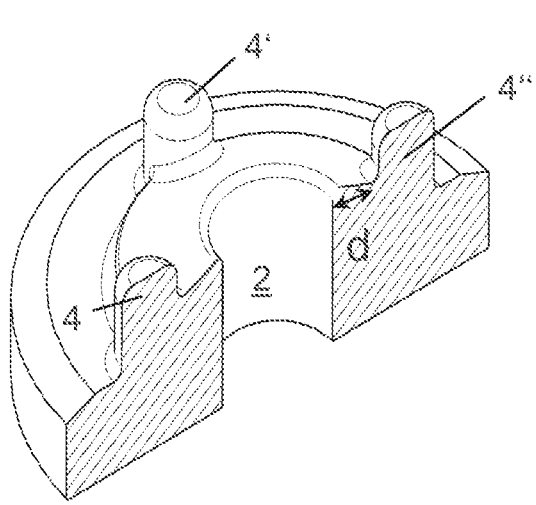
FIGS. 8A-8D: perspective sectional views of additional embodiments of the device according to the invention with four projections in the area of a secondary channel leading into the main channel.
Figure 8B:
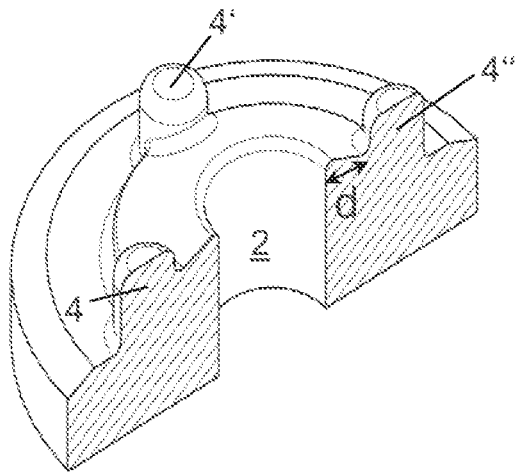
Figure 8C:
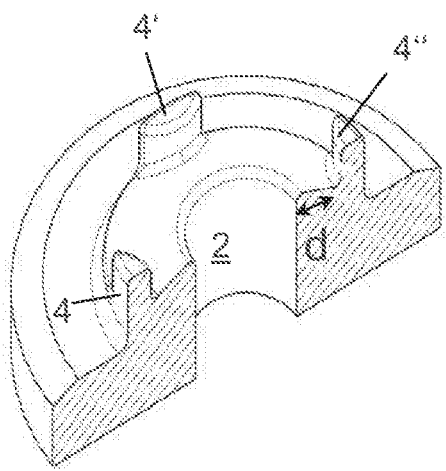
Figure 8D:
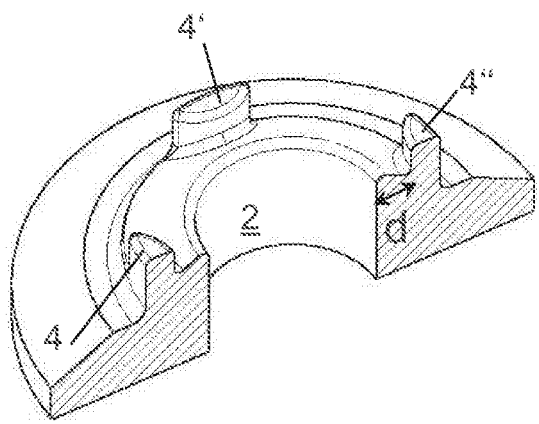

In FIGS. 7A and 7B, a preferred embodiment of the device according to the invention with two projections 4, 4' is represented, which are arranged at diametrically opposite sites of the opening 2a of a secondary channel 2. In it the two projections 4, 4' are located at a predetermined distance d from the outer circumferential margin (at the opening diameter D) of the opening 2a, i.e., the outer surface of each projection 4, 4' is at a predetermined distance d from the opening margin. This distance d is advantageously in the range from 0.5 to 2 mm and preferably approximately 1.3 mm. Here the height A of the projection is advantageously in the range from 0.2 to 0.7 mm and preferably approximately 0.5 mm (FIG. 7A). The channel wall 2c is here advantageously beveled downward towards the exterior, as shown in FIG. 7A.

In FIGS. 8A to 8D, different embodiments of the device according to the invention in each case with a total of four projections 4 are represented (of which only three projections 4, 4', 4" are shown in the perspective sectional view), which each have different shapes and are distributed evenly in the circumferential direction (i.e., at angular separations of 90°) around the opening margin, and arranged at different distances d from the (radially external) opening margin in the different embodiments of FIGS. 8A to 8D.

In FIGS. 9A-9D, perspective sectional views of other embodiments of the device according to the invention are shown (FIGS. 9A to 9D), in which several projections 4 are arranged at a distance from one another on the channel wall 2c of a secondary channel 2 leading into the main channel 1. In these embodiments, the inner circumference of the projections 4 ends flush with the (radially external) opening margin, i.e., there is no separating distance between the circumferential margin of the opening 2a and the inner circumference of the projection 4. Each of these projections 4 is here formed (integrally) as a protrusion on the upper side of the channel wall 2c of the secondary channel 2. The channel wall 2c is here advantageously beveled downward towards the exterior, as shown in FIGS. 9A to 9D. In the embodiments of FIGS. 9A to 9D, a lowest level N of opening 2a is obtained by the projections 4 formed as a protrusion on the upper side of the channel wall 2c of the secondary channel 2. The area of the opening 2a, which, viewed in the direction of flow of the fluid, first leads into the main channel 1, is considered to be the lowest opening level N. According to the invention, the projections 4 are advantageously located approximately 0.3 to 0.5 mm over the lowest opening level N.

The invention is not limited to the described embodiment example and the described application case. In principle, the invention can be used in all devices for transferring fluids, in which the fluid is transferred from a secondary channel into a main channel or vice-versa, and the secondary channel can be closed in a fluid-tight manner by means of a squeeze valve device with a resilient closing element. Such devices are used, for example, in injection apparatuses for the intravenous injection of fluids into the human or animal body or in dialysis apparatuses. In contrast to the above-described embodiment example, it is possible that only one secondary channel is provided, or it is also possible to provide two or even more secondary channels that lead into the main channel. The channels of the device according to the invention are moreover not necessarily formed in the body of a cassette, instead they can also be designed as pipe or hose lines at least in some sections, for example.

What is claimed is:

1. A device for transferring a fluid, said device comprising:
   a main channel;
   a secondary channel leading at an opening thereof into the main channel to enable the fluid to flow in a flow direction from the secondary channel into the main channel; and
   a flexible closing element for closing the secondary channel,
   wherein the opening of the secondary channel can be closed in a fluid-tight manner by pressing the closing element with an external force onto or into the opening,
   at least one projection is associated with the secondary channel, the at least one projection being arranged around the opening of the secondary channel and having a top that protrudes into the main channel and that protrudes over at least one of the opening of the secondary channel and a lowest level of the opening, such that the top of the at least one projection is located in the flow direction of the fluid on a downstream level with respect to the lowest level of the opening, and
   when a negative pressure is present in the main channel and/or in the secondary channel, the closing element rests on the top of the at least one projection when no external force is acting on the closing element, so as to prevent a complete closing of the secondary channel while no external force is acting on the closing element.

2. The device according to claim 1, wherein the closing element is designed so that, during the closing of the secondary channel, the closing element bears against at least one of the opening and the lowest level of the opening, and also bears against the at least one projection which is associated with the secondary channel.

3. The device according to claim 1, wherein the closing element is a flexible membrane or a flexible film which can be pressed by a valve actuator onto or into the opening of the secondary channel.

4. The device according to claim 1,
   wherein the main channel and the secondary channel are formed in a body, and
   the main channel has an opening which is covered by the flexible closing element.

5. The device according to claim 4, wherein the body is a component of an exchangeable cassette for insertion into a fluid-conveying device.

6. The device according to claim 1, wherein the closing element is movable between a base position and a closed position, and the opening of the secondary channel or the lowest level of the opening is open when the closing element is in the base position and closed in a fluid-tight manner when the closing element is in the closed position.

7. The device according to claim 1, wherein the at least one projection comprises at least two projections that are associated with the secondary channel and arranged around the opening of the secondary channel.

8. The device according to claim 7, wherein the at least two projections are distributed evenly around the opening of the secondary channel.

9. The device according to claim 1, wherein the main channel is formed in an area of the secondary channel leading therein in the form of a ring channel which extends in the shape of a ring around a channel wall of the secondary channel.

10. The device according to claim 1, wherein the opening of the secondary channel or the lowest level of the opening is located approximately or exactly in an area of a center plane of the main channel.

11. The device according to claim 1, wherein the at least one projection is cylindrical.

12. The device according to claim 11, wherein the at least one projection is in the shape of a dome, a pin, a column, or a mushroom.

13. The device according to claim 1, wherein, when no external force is acting on the closing element and the negative pressure is not present in the main channel or in the secondary channel, the top of the at least one projection is located below the closing element.

14. The device according to claim 1, wherein the secondary channel is part of a plurality of secondary channels that each lead at an opening into the main channel, and at least one projection is associated with each of the secondary channels and arranged around the opening of that secondary channel with a top that protrudes into the main channel and over the opening of that secondary channel or over a lowest level of the opening.

15. A cassette for insertion into a fluid-conveying device, said cassette comprising:
a body; and
a device for transferring a fluid,
wherein the device for transferring a fluid includes:
a main channel;
a secondary channel leading at an opening thereof into the main channel to enable the fluid to flow in a flow direction from the secondary channel into the main channel; and
a flexible closing element for closing the secondary channel,
wherein the opening of the secondary channel can be closed in a fluid-tight manner by pressing the closing element with an external force onto or into the opening,
at least one projection is associated with the secondary channel, the at least one projection being arranged around the opening of the secondary channel and having a top that protrudes into the main channel and that protrudes over at least one of the opening of the secondary channel and a lowest level of the opening, such that the top of the at least one projection is located in the flow direction of the fluid on a downstream level with respect to the lowest level of the opening, and
when a negative pressure is present in the main channel and/or in the secondary channel, the closing element rests on the top of the at least one projection when no external force is acting on the closing element, so as to prevent a complete closing of the secondary channel while no external force is acting on the closing element.

16. The cassette according to claim 15, wherein the device for transferring a fluid includes:
the secondary channel which is a rinsing secondary channel for supplying a rinsing solution; and
another secondary channel for supplying an active solution, the other secondary channel leading at an opening into the main channel to enable the active solution to flow in a second flow direction from the other secondary channel into the main channel,
wherein at least one other projection is associated with the other secondary channel, the at least one other projection being arranged around the opening of the other secondary channel and having a top that protrudes into the main channel and that protrudes over at least one of the opening of the other secondary channel and a lowest level of that opening, such that the top of the at least one other projection is located in the second flow direction of the active solution on the downstream level with respect to the lowest level of the opening of the other secondary channel.

17. The cassette according to claim 16, wherein the rinsing secondary channel, in an area of an upstream end, leads into the main channel, and, for supplying the active solution, the other secondary channel leads into the main channel further downstream.

18. A fluid-conveying device comprising:
the cassette according to claim 15; and
at least one valve actuator which is movable between a closed position and an open position,
wherein in the closed position, the at least one valve actuator presses the closing element onto or into the opening of the secondary channel so as to close the secondary channel in a fluid-tight manner.

19. The fluid-conveying device according to claim 18, wherein, even when the negative pressure is present in the main channel and/or in the secondary channel, the flexible closing element is raised by a resetting force of the closing element from the opening or from the lowest level of the opening, if the valve actuator is in its open position.

20. A device for transferring a fluid, said device comprising:
a main channel;
at least one secondary channel, each of which leads at an opening thereof into the main channel to enable the fluid to flow in a flow direction from that secondary channel into the main channel; and
a flexible closing element for closing the at least one secondary channel,
wherein the opening of each of the at least one secondary channels can be closed in a fluid-tight manner by pressing the closing element with an external force onto or into the opening,
at least one projection is associated with each of the at least one secondary channels, the at least one projection being arranged around the opening of that secondary channel and having a top that protrudes into the main channel and that protrudes over at least one of the opening of that secondary channel and a lowest level of the opening of that secondary channel, such that the top of the at least one projection is located in the flow direction of the fluid on a downstream level with respect to the lowest level of the opening, and
when a negative pressure is present in the main channel and/or in one of the at least one secondary channels, the closing element rests on the top of the at least one projection when no external force is acting on the closing element, so as to prevent a complete closing of that secondary channel while no external force is acting on the closing element.

* * * * *